United States Patent [19]

Rozen et al.

[11] Patent Number: 5,250,213
[45] Date of Patent: Oct. 5, 1993

[54] 1,1,1,2,2,3,3,4,4,5,6-UNDECAFLUOROHEXANE AND USE THEREOF IN COMPOSITIONS AND PROCESSES FOR CLEANING

[75] Inventors: Shlomo Rozen, Tel-Aviv, Israel; Frank J. Weigert, Wilmington, Del.

[73] Assignee: E. I du Pont de Nemours and Company, Wilmington, Del.

[21] Appl. No.: 695,826

[22] Filed: May 6, 1991

[51] Int. Cl.$^5$ .................. C11D 7/30; C11D 7/50; C07C 19/02; C07C 19/08

[52] U.S. Cl. ......................... 252/162; 252/153; 252/170; 252/171; 252/172; 252/364; 570/134

[58] Field of Search ............... 252/162, 170, 171, 172, 252/364, 153; 570/134

[56] References Cited

U.S. PATENT DOCUMENTS

| | | | |
|---|---|---|---|
| 2,490,764 | 12/1949 | Benning et al. | 570/134 |
| 2,980,740 | 4/1961 | Hasek et al. | 570/142 |
| 2,999,815 | 9/1961 | Eiseman | 252/171 |
| 2,999,817 | 9/1961 | Bower | 252/172 |
| 3,573,213 | 3/1971 | Burt | 252/171 |
| 3,728,268 | 4/1973 | Burt | 252/171 |
| 3,729,567 | 4/1973 | Terrell | 514/816 |
| 3,789,006 | 1/1974 | McMillan et al. | 252/171 |
| 3,799,995 | 3/1974 | Hutchinson | 570/142 |
| 3,881,949 | 5/1975 | Brock | 134/31 |
| 3,903,009 | 9/1975 | Bauer et al. | 252/171 |
| 4,715,900 | 12/1987 | Connon et al. | 134/31 |
| 4,754,085 | 6/1988 | Gervasutti et al. | 570/175 |
| 4,902,838 | 2/1990 | Manzer et al. | 570/151 |
| 4,938,849 | 7/1990 | Davies et al. | 204/73 R |
| 4,947,881 | 8/1990 | Magio et al. | 134/40 |
| 4,954,666 | 9/1990 | Bielefeldt et al. | 570/134 |
| 5,053,155 | 10/1991 | Mahler | 252/68 |
| 5,059,728 | 10/1991 | Li et al. | 570/134 |
| 5,064,559 | 11/1991 | Merchant et al. | 252/171 |
| 5,064,560 | 11/1991 | Merchant | 252/171 |
| 5,073,290 | 12/1991 | Anton et al. | 252/162 |
| 5,076,956 | 12/1991 | Anton | 252/162 |
| 5,118,359 | 6/1992 | Li et al. | 134/42 |
| 5,162,594 | 11/1992 | Krespan | 570/126 |
| 5,171,902 | 12/1992 | Krespan et al. | 570/175 |

FOREIGN PATENT DOCUMENTS

| | | |
|---|---|---|
| 431458 | 6/1991 | European Pat. Off. |
| 1560544 | 3/1969 | France . |
| 8912614 | 12/1989 | PCT Int'l Appl. . |
| 1244256 | 1/1969 | United Kingdom . |

OTHER PUBLICATIONS

Du Pont Freon Solvent Bulletin FS-1.
Du Pont Freon Solvent Bulletin B-7.
Medda et al *J. Indian Chem. Soc.*, vol. LVIII (Nov. 1981) pp. 1044–1047.
Barlow et al., *Heterocyclic Polyfluoro:compounds*, J.C.S. Perkin I pp. 2258–2267, 1980.
S. Rozen et al., *Direct Addition of Elemental Fluorine to Double Bonds*, J. Org. Chem., 1986*, 51, pp. 3607–3611.
L. Conte et al., *Fluorination of Hydrogen–Containing Olefins with Elemental Fluorine*, Journal of Fluorine Chemistry, 38 (1988)*, pp. 319–326.

*Primary Examiner*—Linda Skaling

[57] ABSTRACT

The compound, 1,1,1,2,2,3,3,4,4,5,6-undecafluorohexane, and mixtures thereof with alcohols, ethers, esters, ketones, nitromethane, and halogenated hydrocarbons are disclosed; as is the use thereof for cleaning a solid surface by treating the surface with said compound or said mixtures.

6 Claims, No Drawings

1,1,1,2,2,3,3,4,4,5,6-UNDECAFLUOROHEXANE AND USE THEREOF IN COMPOSITIONS AND PROCESSES FOR CLEANING

FIELD OF THE INVENTION

This invention relates to halogen substituted hydrocarbon compounds, their compositions and uses, and more particularly to fluorine-substituted hydrocarbons, their mixtures with solvents, such as ethanol or methanol, and the use thereof for cleaning solid surfaces.

BACKGROUND OF THE INVENTION

Various organic solvents have been used as cleaning liquids for the removal of contaminants from contaminated articles and materials. Certain fluorine-containing organic compounds, such as 1,1,2-trichloro-1,2,2-trifluoroethane, are useful for this purpose, particularly with regard to cleaning organic polymers and plastics which may be sensitive to other more common and more powerful solvents such as trichloroethylene or perchloroethylene. Recently, however, there have been efforts to reduce the use of certain compounds such as trichlorotrifluoroethane (which contain chlorine) because of a concern over their potential to deplete ozone, and to affect thereby the layer of ozone that is considered important in protecting the Earth's surface from ultraviolet radiation.

Boiling point, flammability, and solvent power can often be adjusted by preparing mixtures of solvents. For example, certain mixtures of 1,1,2-trichloro-1,2,2-trifluoroethane with other solvents (e.g., isopropyl alcohol and nitromethane) have been reported as useful in removing contaminants that are not removed by 1,1,2-trichloro-1,2,2-trifluoroethane alone, and in cleaning articles, such as electronic circuit boards, where the requirements for a cleaning solvent are relatively stringent (i.e., it is generally desirable in circuit board cleaning to use solvents that have low boiling points, are non-flammable, have low toxicity, and have high solvent power so that flux (such as rosin) and flux residues which result from soldering electronic components to the circuit board, can be removed without damage to the circuit board substrate).

Whereas boiling point, flammability, and solvent power can often be adjusted by preparing mixtures of solvents, the utility of the resulting mixtures can be enhanced for certain applications if the mixtures do not fractionate to an undesirable degree during use and recovery or reuse. Azeotropic compositions, with their constant boiling points and constant composition characteristics, are thus considered particularly useful.

A number of compositions using halohydrocarbons containing fluorine have been discovered and in some cases used as solvents for the removal of solder fluxes and flux residues from printed circuit boards and for miscellaneous vapor degreasing applications. For example, U.S. Pat. No. 2,999,815 discloses the azeotrope of 1,1,2-trichloro-1,2,2-trifluoroethane with acetone; U.S. Pat. No. 3,903,009 discloses a ternary azeotrope of 1,1,2-trichloro-1,2,2-trifluoroethane with nitromethane and ethanol; U.S. Pat. No. 3,573,213 discloses an azeotrope of 1,1,2-trichloro-1,2,2-trifluoroethane with nitromethane; U.S. Pat. No. 3,789,006 discloses the ternary azeotrope of 1,1,2-trichloro-1,2,2-trifluoroethane with nitromethane and isopropyl alcohol; U.S. Pat. No. 3,728,268 discloses the ternary azeotrope of 1,1,2-trichloro-1,2,2-trifluoroethane with acetone and ethanol; U.S. Pat. No. 2,999,817 discloses the binary azeotrope of 1,1,2-trichloro-1,2,2-trifluoroethane and methylene chloride; and U.S. Pat. No. 4,715,900 discloses ternary compositions of trichlorotrifluoroethane, dichlorodifluoroethane, and ethanol or methanol.

As noted above, many solvent compositions which have proven useful for cleaning contain at least one component that is a halogen-substituted hydrocarbon containing chlorine, and concerns have been raised over the ozone depletion potential of halogen-substituted hydrocarbons that contain chlorine. Efforts are being made to develop compositions that may at least partially replace the chlorine-containing components with other components having lower potential for ozone depletion.

Various methods of preparing organic compounds containing fluorine are known. The fluorination of double bonds with elemental fluorine has been discussed in S. Rozen, et al., J. Org. Chem., 51, 3607 (1986); L. Conte, et al., J. Fluorine Chem., 38, 319 (1988); and C. Gervasutti, et al., U.S. Pat. No. 4,754,085 (1988).

SUMMARY OF THE INVENTION

This invention provides a novel fluorohydrocarbon compound, 1,1,1,2,2,3,3,4,4,5,6-undecafluorohexane, and mixtures thereof with miscible solvents such as alcohols (e.g., methanol, ethanol, etc.), ethers (e.g., tetrahydrofuran, etc.), esters, ketones (e.g., acetone), nitromethane, and halogenate hydrocarbons (e.g., 1,2-dichloroethylene, etc.). The compound, 1,1,1,2,2,3,3,4,4,5,6-undecafluorohexane, and its compositions with such solvents are well suited for solvent cleaning applications. Mixtures in which none of the components contain chlorine are preferred.

DETAILED DESCRIPTION OF THE INVENTION

A novel fluorohydrocarbon compound, 1,1,1,2,2,3,3,4,4,5,6-undecafluorohexane (i.e., $CF_3CF_2CF_2CF_2CHFCH_2F$), is provided in accordance with this invention. The designation of this compound in conventional nomenclature for halogen-substituted hydrocarbons containing fluorine is HFC-54-11qe. HFC-54-11qe may be prepared by dissolving the olefin, 3,3,4,4,5,5,6,6,6-nonafluoro-1-hexene, in trichlorofluoromethane, cooling the solution to $-78°$ C., and bubbling a mixture of fluorine in nitrogen through the cooled solution of olefin. After reaction, the product may be isolated by washing with bicarbonate and then with water, drying over magnesium sulfate, and distilling to give pure HFC-54-11qe with a one degree boiling point range. 3,3,4,4,5,5,6,6,6-Nonafluoro-1-hexene (i.e., HFC-1549zf, $CF_3CF_2CF_2CF_2CH=CH_2$) is commercially available and may be prepared according to the method disclosed in British Patent Specification 1,244,256. HFC-54-11qe is a liquid under ambient conditions and is considered useful as a solvent for cleaning contaminants from solid substrates.

HFC-54-11qe is miscible with various solvents conventionally used in cleaning operations. Compositions which are suitable for use in cleaning operations and which comprise a mixture of HFC-54-11qe with one or more compounds selected from the group consisting of alcohols, ethers, esters, ketones, nitromethane, and halogenated hydrocarbons, can thus be prepared. The preferred alcohols and halogenated hydrocarbons contain from 1 to 4 carbon atoms; the preferred ethers contain from 2 to 4 carbon atoms; and the preferred esters and ketones contain from 3 to 4 carbon atoms. Examples of suitable alcohols include methanol and ethanol. An example of a suitable ether is tetrahydrofuran. An example of a suitable ketone is acetone. The preferred halogenated hydrocarbons contain hydrogen as well as chlorine and/or fluorine. An example of a suitable halogenated hydrocarbon is 1,2-dichloroethylene. Preferably, such compositions contain at least about 5 percent by weight of HFC-54-11qe and can contain up to 95 percent by weight, or even more, of HFC-54-11qe. Most preferred with respect to ozone depletion potential are compositions in which none of the components contain chlorine.

A composition, which comprises an admixture of effective amounts of HFC-54-11qe and one or more solvents selected from the group consisting of alcohols, ethers, esters, ketones, nitromethane and halogenated hydrocarbons to form an azeotrope or azeotrope-like mixture, are considered especially useful. By azeotrope or azeotrope-like is meant constant boiling liquid admixtures of two or more substances, which admixtures behave like a single substance in that the vapor produced by partial evaporation or distillation has the same composition as the liquid (i.e., the admixtures distill without a substantial change in composition). Constant boiling compositions characterized as azeotropes or azeotrope-like exhibit either a maximum or minimum boiling point as compared with that of nonazeotropic mixtures of the same substances. By effective amounts is meant the amounts of each component of the admixture of the instant invention, which, when combined, results in the formation of the azeotrope or azeotrope-like admixture of the instant invention.

Compositions that are mixtures of HFC-54-11qe with alcohol selected from the group consisting of methanol and ethanol are preferred. HFC-54-11qe, its mixtures with methanol and ethanol, and other mixtures of this invention are useful in a wide variety of processes for cleaning solid surfaces, which comprise treating said surface therewith. Applications include removal of flux and flux residues from printed circuit boards contaminated therewith. As an example, compositions provided in accordance with this invention can be used in cleaning processes such as is described in U.S. Pat. No. 3,881,949 and U.S. Pat. No. 4,715,900, both of which are incorporated herein by reference. Azeotropic compositions permit easy recovery and reuse of the solvent from vapor defluxing and degreasing operation because of their azeotropic nature.

The compositions of this invention may be used in conventional apparatus, employing conventional operating techniques. The solvent(s) may be used without heat if desired, but the cleaning action of the solvent(s) may be assisted by conventional means (e.g., heating, agitation, etc.). In some applications (e.g., removing certain tenacious fluxes from soldered components) it may be advantageous to use ultrasonic irradiation in combination with the solvent(s).

The mixtures of the instant invention can be prepared by any convenient method including mixing or combining the desired amounts of the components. A preferred method is to weigh the desired amounts of each component and thereafter combine them in an appropriate container.

Practice of the invention will become further apparent from the following non-limiting examples.

EXAMPLE 1

The olefin, 3,3,4,4,5,5,6,6,6-nonafluoro-1-hexene, $C_4F_9CH=CH_2$ (40 mL) was dissolved in 400 mL of $CFCl_3$ and cooled to $-78°$ C. A mixture of 6% $F_2$ in $N_2$ was prepared and bubbled through the cold olefin solution at the rate of 350 mL/min. A total of 290 mmol of fluorine was used. The reaction mixture was washed with sodium bicarbonate solution, and then water. The washed mixture was dried over anhydrous $MgSO_4$, and distilled. The product was collected at about $87°-88°$ C. (atmospheric pressure). $^1H$ NMR 4.6–5.3 ppm (m); $^{19}F$ NMR 81.5 (3F, b singlet), 121–128.5 (6F, m), 208.0 (1F, m), 236.7 ppm (1F, triplet, m); MS m/e 245 (M-F-HF)+; 95 ($CF_2CH=CH_2$ or $CF_2CH=CHF$)+; both resulting from allylic cleavage after HF elimination. The average yield of three runs was about 50%.

EXAMPLE 2

The miscibility of HFC-54-11qe with the organic solvents methanol, ethanol, nitromethane, tetrahydrofuran, acetone, and cis-1,2-dichloroethylene, was respectively demonstrated by mixing 5 μL of HFC-54-11qe with 100 μL of each solvent and mixing 5 μL of each of the organic solvents with 100 μL of HFC-54-11qe. Complete miscibility was observed in all twelve cases.

Particular embodiments of the invention are included in the examples. Other embodiments will become apparent to those skilled in the art from a consideration of the specification or practice of the invention disclosed herein. It is understood that modifications and variations may be practiced without departing from the spirit and scope of the novel concepts of this invention. It is further understood that the invention is not confined to the particular formulations and examples herein illustrated, but it embraces such modified forms thereof as come within the scope of the following claims.

What is claimed is:
1. The compound 1,1,1,2,2,3,3,4,4,5,6-undecafluorohexane.
2. A cleaning composition consisting essentially of (i) between about 5 and 95 percent by weight 1,1,1,2,2,3,3,4,4,5,6-undecafluorohexane and (ii) at least one solvent selected from the group consisting of alcohols containing from 1 to 4 carbon atoms, esters containing from 3 to 4 carbon atoms, ethers containing from 2 to 4 carbon atoms, ketones containing from 3 to 4 carbon atoms, halogenated hydrocarbons containing from 1 to 4 carbon atoms, and nitromethane; said at least one solvent being present in an amount which is miscible with said 1,1,1,2,2,3,3,4,4,5,6-undecafluorohexane.
3. The cleaning composition of claim 2 in which none of the components contain chlorine.
4. The cleaning composition of claim 2 which consists essentially of 1,1,1,2,2,3,3,4,4,5,6-undecafluorohexane and at least one solvent selected from the group consisting of methanol, ethanol, tetrahydrofuran, acetone, and 1,2-dichloroethylene.
5. The cleaning composition of claim 4 in which none of the components contain chlorine.
6. The cleaning composition of claim 2 which consists essentially of 1,1,1,2,2,3,3,4,4,5,6-undecafluorohexane and at least one alcohol selected from the group consisting of methanol and ethanol.

* * * * *